US005504237A

United States Patent [19]
Lennon

[11] Patent Number: 5,504,237
[45] Date of Patent: Apr. 2, 1996

[54] PLA₂ INHIBITORS

[75] Inventor: Patrick J. Lennon, Clayton, Mo.

[73] Assignee: Monsanto Company, St. Louis, Mo.

[21] Appl. No.: 429,972

[22] Filed: Apr. 27, 1995

Related U.S. Application Data

[60] Division of Ser. No. 259,720, Jun. 14, 1994, Pat. No. 5,434,288, which is a continuation-in-part of Ser. No. 984,022, Dec. 1, 1992, abandoned.

[51] Int. Cl.⁶ .................................. C07F 9/40; C07F 9/38
[52] U.S. Cl. .................. 558/161; 562/13; 562/21
[58] Field of Search .............................. 558/161; 562/13, 562/21

[56] References Cited

U.S. PATENT DOCUMENTS

| | | | |
|---|---|---|---|
| 4,818,774 | 4/1989 | Kem ........................................ | 558/161 X |
| 5,043,330 | 8/1991 | Nguyen et al. ......................... | 514/107 |
| 5,112,864 | 5/1992 | Djuric et al. . | |
| 5,135,941 | 8/1992 | Djuric et al. . | |
| 5,204,336 | 4/1993 | Kruse et al. ........................... | 558/161 X |

FOREIGN PATENT DOCUMENTS

| | | |
|---|---|---|
| 195097A1 | 9/1986 | European Pat. Off. . |
| 207599A1 | 1/1987 | European Pat. Off. . |
| 3203307 | 7/1983 | Germany . |
| 9231085 | 11/1983 | Germany . |

OTHER PUBLICATIONS

Zupan, L. A. et al., "Calcium is Sufficient But Not Necessary for Activation of Sheep Platelet Cytostolic Phospholipase A₂", *FEBS Letters*, vol. 284, No. 1, 27–30 (1991).
Buckle, D. R., "Synthesis of Aryloxy Analogues of Arachidonic Acid via Wittig and Palladium–catalysed Cross–coupling Reactions", *J. Chem. Research* (S), 1987, pp. 394–395.
Foster, K. A., "Arachidonic Acid Analogues as Inhibitors of of Phospholipase A₂ Activity", vol. 15, pp. 418–419 (1987).
Reid, I. R. et al., "Two-Year Follow-up of Biphosphonate (APD) Treatment in Steroid Osteoporosis", *The Lancet*, 1988, p. 1144.
Creary, X. et al., J. Am. Chem. Soc. 1983, 105 (9), 2851-8.
Yuan, C. et al., Phosphorus, Sulfur Silicon Relat. Elem. 1992, 69 (1–2), 75–81' Chem. Abstr. 117(17): 171559c.
Moskovin, A. V. et al., Zh. Obshch. Khim 1984, 54(10). 2223–37' Chem. Abstr. 102(17)" 149357d.
Robinson, C. N. et al., J. Org. Chem. 1987. 52(10). 2011–15' QD241/06.

Lehnert, W. Tetrahedron 1974. 30(2). 301–5; QD241.T4.
Kosolapoff, G. M. Organophospherus Compounds; John Wiley and Sons: New York, 1950; pp. 113–120; QD412.P1K5.

Primary Examiner—Johann Richter
Assistant Examiner—Michael G. Ambrose
Attorney, Agent, or Firm—Kenneth D. Goetz

[57] ABSTRACT

PlA₂ inhibitors selected from the group consisting of

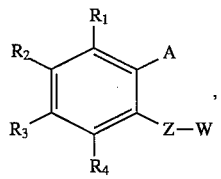

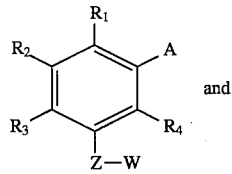

and

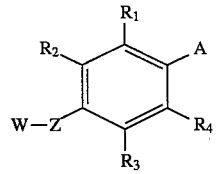

wherein A is selected from the group consisting of

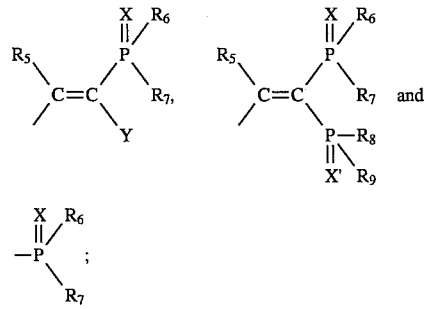

and Z, W, $R_1$, $R_2$, $R_3$, $R_4$, $R_5$, $R_6$, $R_7$, $R_8$, $R_9$, X, X' and Y are as defined herein.

19 Claims, No Drawings

PLA₂ INHIBITORS

This application is a divisional of U.S. Ser. No. 08/259,720 filed Jun. 14, 1994, now U.S. Pat. No. 5,434,288, which is a CIP of U.S. Ser. No. 07/984,022 filed Dec. 1, 1992, now abandoned.

BACKGROUND OF THE INVENTION

This invention relates to $PLA_2$ inhibitors. In one aspect, this invention relates to a method of inhibiting $PLA_2$ using the $PLA_2$ inhibitors of the invention. In another aspect, this invention relates to a method of inhibiting calcium-independent $PLA_2$ using the $PLA_2$ inhibitors of the invention.

Phospholipases $A_2$ are a diverse group of esterases which specifically hydrolyse the sn-2 ester of membrane and other phospholipids. Both calcium dependent and independent examples are known. These enzymes are principally responsible for the release of arachidonic acid during signal transduction in mammalian cells. As such their modulation and inhibition are of potential therapeutic value in treating many diseases and conditions where arachidonic acid, lysophospholipids, and their metabolites (prostaglandins, leukotrienes, thromboxanes, platelet activating factor, etc.,) are responsible for the deleterious effects of these conditions and diseases.

In some circumstances it may be beneficial to inhibit more than one phospholipase $A_2$, particularly in cases where inhibition of the production of early as well as late mediators can be important in controlling pathology, or where inhibition of signalling events can be combined with inhibition of release of arachidonic acid stores.

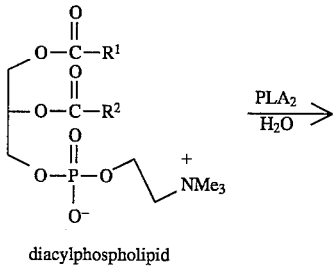

diacylphospholipid

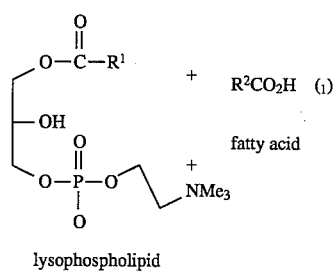

lysophospholipid

Evidence has accumulated for a potential role of $PLA_2$ in myocardial injury to the ischemic heart.

Lysophospholipids have also been implicated as potential mediators of sudden cardiac death, Corr et al, "Lethal Arrhythmias Resulting from Myocardial Ischemia and Infarction", Rosen & Patti, eds., Kluwer Academic Publishers, Boston, 91–014 (1989). The addition of lysophospholipids to normoxic myocardial tissue in vitro induces electrophysiological alterations that are similar to those observed in the ischemic heart in vivo Corr et al, Circ. Res, 55, 135–54 (1984).

Most importantly, lysophospholipid accumulation in the ischemic dog heart in vivo has been correlated with the frequency of cardiac arrhythmias, Kinnaird et al, Lipids, 23, 32–35 (1988). Furthermore, it is known that the carnitine acyltransferase 1 inhibitor, 2-[5-(4-chlorophenyl)-pentyl]-oxirane-2-carboxylate (POCA), prevents the onset of ventricular fibrillation and ventricular tachycardia and inhibits the accumulation of lysophospholipids (and long-chain acylcarnitines) in the ischemic cat heart in vivo, Corr et al, J. Clin. Invest., 83, 927–36 (1989).

Accelerated phospholipid catabolism by $PLA_2$ has also been implicated as a cause of infarct damage in the ischemic heart. In the/ischemic heart, ATP levels decrease. Treatment of rat neonatal myocytes with the glycolytic inhibitor iodoacetate lowers the levels of ATP which results in the release of arachidonic acid and morphological alterations of the myocytes, Chien et al, J. Clin. Invest., 75, 1770–80 (1985). One $PLA_2$ inhibitor (U26,384) prevented the release of arachidonic acid, phospholipid degradation, sarcolemmal membrane defects and the release of creatine kinase that was induced by the treatment of rat neonatal myocytes with iodoacetate, Sen et al, J. Clin. Invest., 82, 1333–38 (1988).

$LTB_4$ is an arachidonic acid metabolite which is produced by the 5-lipoxygenase pathway. Pharmacologically, $LTB_4$ is an important mediator of inflammation. $LTB_4$ is known to induce chemotaxis, chemokinesis, aggregation, and degranulation of leukocytes in vitro, and to induce accumulation of polymorphonuclear leukocytes, and increase vascular permeability and edema formation in vivo. Particularly high levels of $LTB_4$ are detected in lesions in inflammatory diseases such as rheumatoid or spondylarthritis, gout, psoriasis, ulcerative colitis, Crohn's disease, multiple sclerosis and some respiratory diseases. Since the compounds herein inhibit $PLA_2$ and thereby $LTB_4$ synthesis, the compounds of the present invention are useful in treating inflammatory conditions in mammals such as rheumatoid arthritis, inflammatory bowel disease, psoriasis and the like.

Therefore, compounds which inhibit $PLA_2$ provide potential therapeutic approaches to the prevention of arrhythmia, infarct damage, sudden death, and inflammatory conditions, i.e., conditions mediated by inflammatory mediators such as prostaglandins and leukotrienes.

SUMMARY OF THE INVENTION

It is an object of the invention to provide novel $PLA_2$ inhibitors. It is a further object of the invention to provide a method for inhibiting $PLA_2$ using the $PLA_2$ inhibitors of the invention. It is a still further object of the invention to provide a method for inhibiting calcium-independent $PLA_2$ using the $PLA_2$ inhibitors of the invention. It is yet a further object of the invention to provide novel intermediates useful in the preparation of the $PLA_2$ inhibitors of the invention.

According to the invention, $PLA_2$ inhibitors are provided comprising a compound selected from the group consisting of

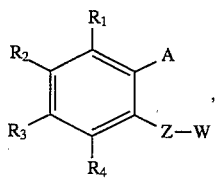

,

3

-continued

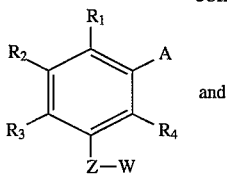

and

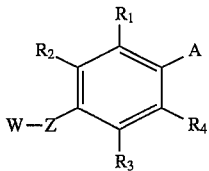

wherein A is selected from the group consisting of

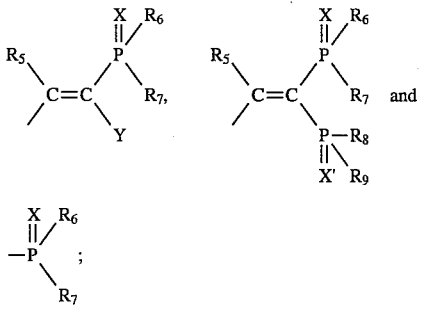

Z is selected from the group consisting of a direct bond and substituted or unsubstituted alkynyl, alkenyl, alkyl and dienyl groups wherein the substituent is selected from the group consisting of —COR, hydroxy alkyl, —SO$_2$R and —PO(OR)(OR') groups;

W is selected from the group consisting of hydrogen and substituted or unsubstituted alkyl, alkenyl, alkynyl, aryl, alkaryl and heteroaryl groups wherein the substituent is selected from the group consisting of —COR, hydroxy, halogen, trifluoromethyl, —NHCOR, —NR'COR, amino, —NR'SO$_2$R and —NHSO$_2$R groups;

wherein the sum of the number of carbon atoms in Z and W is at least 3, preferably about 8 to about 20; $R_1$, $R_2$, $R_3$, $R_4$ and $R_5$ are independently selected from the group consisting of hydrogen, halogen, alkyl, alkenyl, alkynyl, aryl, heteroaryl, alkaryl, alkoxy, thioalkyl, —CHO, —COR, —COOH, —NH$_2$, —NHR, —NRR', —SH, —OH, —COOR, —SO$_2$R, —SOR, —SO$_2$OR, —P(O)(OR)(OR') and —OP(O)(OR)(OR');

X and X' are independently selected from the group consisting of oxygen and sulfur atoms; Y is selected from the group consisting of hydrogen, —CHO, —COOH, —COOR, —CONH$_n$R$_{2-n}$, —CONHOH, —CN, —COSH, —COSR, —CSOH and —CSOR wherein R and R' are independently selected from the group consisting of alkyl, alkenyl, alkynyl, aryl, alkaryl, aralkyl, cycloalkyl, cycloalkenyl and cycloalkynyl groups and n is an integer from 0 to 2;

$R_6$ and $R_7$ are independently selected from the group consisting of alkyl, alkenyl, alkynyl, alkoxy, aryloxy, hydroxy, amino, alkylamino, —SH, thioalkyl, thioaryl, halogen and —OM wherein M is a pharmaceutically acceptable cation or $R_6$ and $R_7$ can form a cyclic or bicyclic structure;

$R_8$ and $R_9$ are independently selected from the group consisting of alkyl, alkenyl, alkynyl, alkoxy, aryloxy, hydroxy, amino, alkylamino, —SH, thioalkyl, thioaryl, halogen and —OM or $R_8$ and $R_9$ can form a cyclic or bicyclic structure; and pharmaceutically acceptable salts thereof.

The number of carbon atoms in $R_6$, $R_7$, $R_8$ or $R_9$ is 0 to about 8, preferably 0 to 2, and most preferably 1 to 2.

4

Further according to the invention, a method of inhibiting PLA$_2$ is provided which comprises utilizing an effective inhibitory amount of a PLA$_2$ as defined herein.

Still further according to the invention, intermediates for use in the preparation of PLA$_2$ are provided comprising a compound selected from the group consisting of

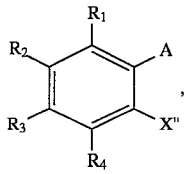

,

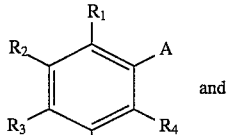

and

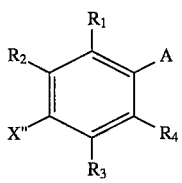

wherein A, $R_1$, $R_2$, $R_3$ and $R_4$ are as defined herein and X" is a halogen.

DETAILED DESCRIPTION OF THE INVENTION

A first embodiment of the invention relates to compounds selected from the group consisting of

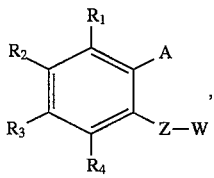

,

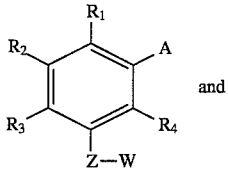

and

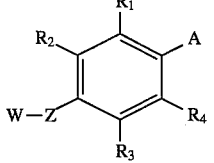

wherein A, Z, W, $R_1$, $R_2$, $R_3$ and $R_4$ are as defined above.

As utilized herein, the term "alkyl" means a linear or branched alkyl radical having 1 to about 20 carbon atoms, preferably about 2 to about 15 carbon atoms. The term "alkenyl" means a linear or branched alkyl radical having 2 to about 20 carbon atoms having ethylenic unsaturation. The term "alkynyl" means a linear or branched alkyl radical having 2 to about 20 carbon atoms having ethynyl unsaturation. The term "dienyl" means a linear or branched diene having cumulated or noncumulated double bonds. Examples of such alkyl, alkenyl, alkynyl and allenyl radicals include ethyl, n-propyl, isobutyl, t-butyl, sec-butyl, n-butyl, pentyl, isoamyl, hexyl, octyl, methyl, 1-propenyl, 2-propenyl, 2-isobutenyl, 1-pentenyl, 1-hexenyl, 1-octenyl, 1-tridecenyl, ethynyl, 1-butynyl, 1-hexynyl, 1-octynyl, 1-tridecynyl, 1,3-decadienyl, 1,3-butadienyl, 1,4-pentadienyl, 2-methyl-1,3-butadienyl, 1,2-propadienyl and 2,3-pentadienyl The term "aryl" alone or in combination, means a phenyl or naphthyl radical. The term "alkaryl" means an aryl radical as defined above which is substituted by an alkyl radical as defined above. The term "heteroaryl" is an aromatic monocyclic, bicyclic or tricyclic heterocycle which contains one or more heteroatoms. Examples of such heteroaryl radicals include pyridyl, quinolyl, furyl, thienyl and oxazolyl. The terms "alkoxy" and "aryloxy" means an alkyl or aryl ether radical wherein the terms alkyl and aryl have the meanings given above. Examples of alkoxy and aryloxy radicals include methoxy, ethoxy, phenoxy and 2-naphthyloxy The term "cycloalkyl" alone or in combination, means a cycloalkyl radical containing from 3 to about 10 carbon atoms. The term "cycloalkenyl", alone or in combination, means a cycloalkyl radical having 1 or more double bonds. The term "cycloalkynyl", alone or in combination, means a cycloalkyl radical having one or more triple bonds. Examples of cycloalkyl, cycloalkenyl and cycloalkynyl radicals include cyclopentyl, cyclohexyl, cyclooctyl, cyclopentenyl, cyclohexenyl, cyclooctenyl, cyclopentadienyl, cyclohexadienyl and cyclooctynyl. The term "halogen" means chlorine, bromine, fluorine and iodine, preferably bromine and iodine.

The term "pharmaceutically acceptable cation" as used herein refers to cations such as ammonium, sodium, potassium, lithium, calcium, magnesium, ferrous, zinc, copper, manganous, aluminum, ferric, manganic, pentaalkyl-ammonium, and the like. The currently preferred pharmaceutically acceptable cation is sodium.

The subject compounds useful as $PLA_2$ inhibitors can be prepared utilizing the methods set forth below in Examples 1–3, 5, 6, 8–15, 17 and 18.

A second embodiment of the invention relates to a method of inhibiting $PLA_2$ comprising contacting the $PLA_2$ with an effective inhibitory amount of a compound selected from the group consisting of

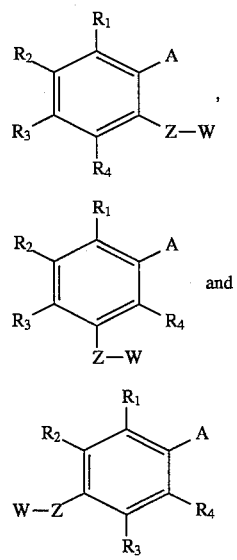

wherein A, Z, W, $R_1$, $R_2$, $R_3$ and $R_4$ are as defined above.

A preferred class of compounds for use in the inhibition of $PLA_2$ is one wherein at least one of Z and W contains at least one carbon-carbon double bond or carbon-carbon triple bond, such as wherein Z is alkenyl or alkynyl and W is hydrogen.

A more preferred class of compounds for use in the method of the present invention is the class wherein $R_1$, $R_2$, $R_3$ and $R_4$ are hydrogen.

A most preferred class of compounds for use in the present invention is the class wherein Y is selected from the group consisting of hydrogen, —COOR and —COOH, $R_6$, $R_7$, $R_8$ and $R_9$ are independently selected from the group consisting of hydroxy, alkoxy and —ONa.

The compounds of the present invention for inhibiting $PLA_2$ can be administered in such oral dosage forms as tablets, capsules, soft gels, pills, powders, granules, elixirs or syrups. The compounds can also be administered intravascularly, intraperitoneally, subcutaneously, intramuscularly, or topically using forms known to the pharmaceutical art. Moreover, they can be administered rectally or vaginally, in such forms as suppositories or bougies. In general, the preferred form of administration is oral.

For the orally administered pharmaceutical compositions and methods of the present invention, the foregoing active ingredients will typically be administered in admixture with suitable pharmaceutical diluents, excipients or carriers (collectively referred to herein as "carrier" materials) suitably selected with respect to the intended form of administration and consistent with conventional pharmaceutical practices.

For example, for oral administration in the form of tablets or capsules, a therapeutically or prophylactically effective amount of one or more compounds of the present invention can be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof. For oral administration in liquid forms, such as in soft gels, elixirs, syrups, drops and the like, a therapeutically or prophylactically effective amount of the active drug components can be combined with any oral nontoxic pharmaceutically acceptable inert carrier such as water, saline, ethanol, polyethylene glycol, propylene glycol, corn oil, cotton seed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethyl cellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methyl cellulose, agar, bentonite, guar gum, and the like, or combination thereof. Sweetening and flavoring agents and preservatives can also be included where appropriate.

For intravascular, intraperitoneal, subcutaneous or intramuscular administration, one or more compounds of the present invention can be combined with a suitable carrier such as water, saline, aqueous dextrose, and the like. For topical administration, therapeutically effective amounts of one or more compounds of the present invention can be combined with pharmaceutically acceptable creams, oils, waxes, gels, and the like. Regardless of the route of administration selected, the compounds of the present invention are formulated into pharmaceutically acceptable dosage forms by conventional methods known to those skilled in the art. The compounds can also be formulated using pharmacologically acceptable base addition salts. Moreover, the compounds or their salts may be used in a suitable hydrated form.

Regardless of the route of administration selected, a nontoxic but therapeutically or prophalactically effective quantity of one or more compounds of this invention is employed in any treatment associated with the inhibition of $PLA_2$.

As used herein, the term "pharmaceutically acceptable salts" refers to pharmacologically acceptable base addition salts derived from pharmaceutically acceptable nontoxic inorganic or organic bases. Among the inorganic bases employed to produce pharmaceutically acceptable salts are the hydroxide bases of the "pharmaceutically acceptable cations" disclosed above. Among the organic bases employed to produce pharmaceutically acceptable salts are the pharmaceutically acceptable nontoxic bases of primary, secondary and tertiary amines. Especially preferred nontoxic bases are isopropyl amine, diethyl amine, ethanol amine, dicyclohexyl amine, choline and caffeine.

All of the pharmaceutically acceptable nontoxic addition salts are prepared by conventional processes which are well known to those of ordinary skill in the art.

A third embodiment of the invention relates to intermediates for use in the preparation of the $PLA_2$ inhibitors of the invention. The intermediates are compounds selected from the group consisting of

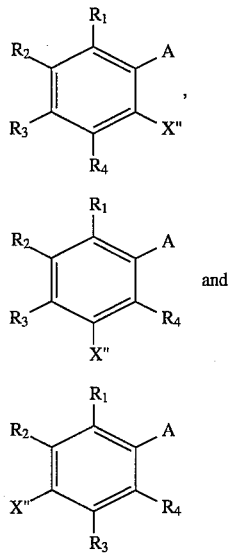

wherein A, $R_1$, $R_2$, $R_3$ and $R_4$ are as defined above and X" is a halogen, preferably bromine or iodine.

A preferred class of intermediates for use in the present invention is one wherein $R_1$, $R_2$, $R_3$ and $R_4$ are hydrogen.

A most preferred class of intermediates is the class wherein Y is selected from the group consisting of hydrogen, —COOR and —COOH, and $R_6$, $R_7$, $R_8$ and $R_9$ are independently selected from the group consisting of hydroxy, alkoxy and —ONa.

The subject intermediates can be prepared utilizing the methods set forth below in Examples 4, 7 and 16.

In the following examples, all reagents were used as received without purification. All proton and carbon NMR spectra were obtained on either a Varian VXR-300 or VXR-400 nuclear magnetic resonance spectrometer.

EXAMPLES

Example 1

Tetraethyl [2-[3-(1-tridecynyl)phenyl]ethenyltdene]bisphosphonate

In a three neck round bottom flask fitted with an argon inlet, dropping funnel, magnetic stir bar, and septum, tetrahydrofuran (anhydrous, 50 ml) was introduced and cooled to 0° C. Titanium tetrachloride (2.73 ml, 24.9 mmol) dissolved in dry carbon tetrachloride (6.8 ml) was added dropwise over a 20 minute period, producing a copious yellow precipitate. 3-(1-Tridecynyl)benzaldehyde prepared according to the method described in EP 195 097 A1, which is incorporated by reference herein, (3.52 g, 12.37 mmol) was then added via cannula over a ten minute period. A few milliliters of tetrahydrofuran was used to rinse the aldehyde containing flask into the reaction flask. Tetraethylmethylenediphosphonate (3.55 g, 12.37 mmol) was added via cannula over a two to three minute period. N-Methyl morpholine (anhydrous, 5.46 ml, 49.7 mmol) in dry tetrahydrofuran (8.4 ml) was added dropwise over a forty five minute period. The reaction was stirred for 3.5 hours at 0° C. At the end of this time, water (14 ml) was added dropwise over a few minutes to the reaction mixture at 0° C. Ether (25 ml) was added to the mixture which was shaken, and the layers were separated. The aqueous layer was extracted with two more portions of ether (25 ml). The combined organic layers were washed with saturated aqueous sodium chloride solution (25 ml), saturated aqueous sodium bicarbonate solution (25 ml), and with saturated sodium chloride solution (25 ml). After drying ($MgSO_4$), the organic phase was filtered and stripped down to a brown-orange liquid. This liquid was chromatographed on silica (0.4 kg) eluting with 80% hexane, 15% ethyl acetate, and 5% ethanol to give the product as a pale yellow liquid, 4.65 g, 8.38 mmol, 67.8% yield; $^1$H NMR ($CDCl_3$) δ0.88 (m, 3 H), 1.12 to 1.67 (several m, 30 H), 2.37 (t, J= 7.1 Hz, 2 H), 4.06 (m, 4 H), 4.21 (m, 4 H), 7.31 (m, 1 H), 7.41 (d, J=7.7 Hz, 1 H), 7.68 (m, 2 H), 8.25 (dd, J=47.5, 28.9 Hz, 1 H); FAB mass spectrum m/z 561 (M+ Li)$^+$.

Example 2

[2-[3-(1-Tridecynyl)phenyl]ethenylidene]bisphosphonic acid

Tetraethyl [2-[3-(1-tridecynyl)phenyl] ethenylidene]bisphosphonate (3,247 g, 5.85 mmol) prepared according to Example 1 was dissolved in a mixture of $CH_2Cl_2$—$CD_2Cl_2$ (25 ml, 4:1), and stirred under argon while trimethylsilyl bromide (3.5 ml, 26.5 mmol) was added. After the reaction was stirred for 6.5 hours, the solvent was removed under reduced pressure and the residue was briefly placed on the vacuum line. Hydrolysis was effected in tetrahydrofuran-water (9:1, 10 ml), stirring for 39 hours at room temperature. After stripping off the solvent, the residue was recrystallized from heptane-ether to give the product as a white solid, 0,416 g, 0.94 mmol, 16% yield; $^1$H NMR ($CD_3OD$) ∂0.89 (t, J=6.9 Hz, 3 H), 1.21 to 1.65 (several m, 18 H), 2.40 (t, J=7.0 Hz, 2 H), 7.55 (m, 2 H), 7.71 (m, 2 H), 8.03 (dd, J=46.1, 29.2 Hz, 1 H); HRMS calcd for (M+H)$^+$ $C_{21}H_{33}O_6P_2$ m/z 443.1752, found 443.1700.

Example 3

Disodium [2-[3-(1-tridecynyl)phenyl]ethenylidene]bisphosphonate

2-[3-(1-Tridecynyl)phenyl]ethenylidene]bisphosphonic acid (0.103 g, 0.223 mmol) prepared according to Example 2 was dissolved in dry tetrahydrofuran (10 ml) and stirred while sodium ethoxide in ethanol (0.177 M, 2.58 ml, 0.457 mmol) was added. After one hour, the solvent was removed under reduced pressure leaving a brownish yellow solid. This solid was powdered and washed successively with anhydrous ether, tetrahydrofuran, acetonitrile, and ethanol leaving a white solid, 43.3 mg, 0.089 mmol, 38% yield; $^1$H NMR (D$_2$O, relative to HOD peak at 4.64) ∂0.76 (t, J=6.9 Hz, 3 H), 1.05 to 1.58 (several m, 18 H), 2.35 (t, J=7.0 Hz, 2 H), 7.30 (m, 2 H), 7.55 (dd, J=43.8, 27.0 Hz, 1 H), 7.69 (m, 2 H); FAB mass spectrum m/z 443 (M−2Na+3H)$^+$, 465 (M−Na+2H)$^+$, 487 (M+H)$^+$.

Example 4

Ethyl 3-(2-bromophenyl)-2-E-(diethoxyphosphinyl)propenoate

2-Bromobenzaldehyde (18.5 g, 100.0 mmol) was added to a 500 ml round bottom flask along with triethyl phosphonoacetate (21 ml, 105.9 mmol). Dry benzene (200 ml) was added, and benzoic acid (0.60 g, 4.9 mmol) and piperidine (0.60 ml, 6.07 mmol). The flask was equipped with a magnetic stir bar, Dean-Stark trap, and reflux condenser. The apparatus was inerted by several cycles of vacuum followed by argon, then connected to a bubbler, and reflux was started. Collection of water in the Dean-Stark trap was very slow and gradual. Additional quantities of piperidine (0.2 ml, 2 mmol) were added on days 2, 5, 10, 12, 19, 21, and 25 (0.1 ml, 1 mmol); Additional quantities of benzoic acid (0.20 g, 1.64 mmol) were added on days 10, 12, 21 and 25 (0.10 g, 0.82 mmol). Reflux was stopped after 26.7 days. After cooling, the reaction mixture was poured into water. The organic phase was washed successively with 0.1 N HCl (2×150 ml), water (150 ml), saturated aqueous sodium bicarbonate (2×150 ml), and water (2×150 ml). After stripping down to an orange oil, the residue was chromatographed on silica eluting with 1:1 ethyl acetate-hexanes. Tlc on silica developed in the same solvent system gave an R$_f$ of 0.22. The product was obtained as a liquid, 7.84 g, 20.0 mmol, 20% yield. $^1$H NMR (C$_6$D$_6$) ∂0.73 (t, J=7 Hz, 3 H), 1.12 (m, 6 H), 3.89 (q, J=7.1 Hz, 4 H), 6.59 (t, J=7.7 Hz, 1 H), 6.76 (t, J=7.6 Hz, 1 H), 7.21 (d, J=8.1 Hz, 1 H), 7.32 (d, J=7.7 Hz, 1 H), 8.16 (d, J=22.7 Hz, 1 H).

Example 5

Ethyl 2-(diethoxyphosphinyl)-3-[2-(1-tridecynyl)phenyl]-2-E-propenoate

Ethyl 3-(2-bromophenyl)-2-E-(diethoxyphosphinyl)propenoate (7.84 g, 20.0 mmol) prepared according to Example 4 was placed in a three neck round bottom flask equipped with a condenser, stir bar, internal thermometer, and argon inlet. 1-Tridecyne (6.30 g, 34.9 mmol) and triphenylphosphine (0.161 g, 0.614 mmol) were added along with triethylamine (110 ml) and the system was degassed by repeated vacuum-argon cycles. Under an argon atmosphere, palladium acetate (0.048, 0.214 mmol) was added, and heating in an oil bath (100°–105° C.) was started. The internal temperature stayed in the range of 89°–92° C. during the reaction. Within a few hours a light precipitate started forming. After about 42 hours, additional tridecyne (1.0 g, 5.5 mmol) was added. The reaction was stopped after 53 hours. After cooling the reaction mixture was filtered and the precipitate was washed with triethylamine. The filtrate was stripped down to a reddish oil. Multiple chromatographies on silica eluting with ethyl acetate in hexane (32% ethyl acetate was best) yielded a yellow liquid, 2.43 g, 5.08 retool, 25.3% yield; $^1$H NMR (CDCl$_3$) ∂0.88 (m, 3 H), 1.17 (t, J=7.2 Hz, 3 H), 1.21 to 1.48 (several m, 22 H), 1.64 (quintet, J=7.5 Hz, 2 H), 2.43 (t, J=7.2 Hz, 2 H), 4.22 (m, 4 H), 7.19 to 7.48 (several m, 4 H), 8.06 (d, J=23.7 Hz, 1 H); CI mass spectrum m/z 491 (M+H)$^+$.

Example 6

Ethyl E-2-phosphono-3-[2-(1-tridecynyl)phenyl]propenoate

Ethyl 2-(diethoxyphosphinyl)-3-[2-(1-tridecynyl)phenyl]-2-E-propenoate (0.50 g, 1.02 mmol) prepared according to Example 5 was dissolved in dry CH$_2$Cl$_2$ (3 ml) and CD$_2$Cl$_2$ (2 ml, dried over activated neutral alumina) and cooled to 0° C. Bromotrimethylsilane (0.31 ml, 2.35 mmol) was added over a two to three minute period. The progress of the reaction was monitored by $^{31}$p NMR, to follow disappearance of the starting material. After about 5 hours, the solvent was removed under reduced pressure. Acetone-heptane (5.5 ml, 10:1) containing 0.045 ml (2.5 mmol) water was added and the reaction was stirred for 1.5 hours. At the end of this time the solvent was strippea. Since NMR indicated incomplete reaction, acetone (5 ml) containing water (0.05 ml, 2.8 mmol) was added and stirring was continued for two hours. After stripping the solvent, the reaction was still incomplete. It required 2.5 more hours under these conditions to complete the reaction. The solvent was stripped off and the residue was chromatographed on silica eluting with 10% chloroform and 20% methanol in heptane. Fractions containing product were recrystallized from heptane yielding a white solid, 0.211 g, 0.486 mmol, 47.6% yield; mp 68°–69° C.; $^1$H NMR (CDCl$_3$) ∂0.86 (m, 3 H), 1.09 to 1.63 (several m, 21 H), 2.40 (t, J=7.1 Hz, 2 H), 4.19 (q, J=7.1 Hz, 2 H), 7.17 to 7.44 (several m, 4 H), 8.15 (d, J=24.7 Hz, 1 H), 8.81 (br s, 2.7 H); FAB mass spectrum m/z 434 (M+ H)$^+$.

Example 7

Diethyl-3-iodophenylphosphonate m-Diiodobenzene (15.15 g, 45.92 mmol) was placed in a 3 neck round bottom flask with a stirring bar. Tetrakis(triethyl phosphite)nickel (14.2 mg, 0.0196 mmol) was added to the flask in the dry box and adapters ending in a receiving flask were added, so as to make a small air cooled distillation assembly. Under argon, the reaction flask was placed in an oil bath at 160° C. The m-diiodobenzene rapidly melted. The receiving flask was placed in a dry ice bath. Triethyl phosphite (8.6 ml, 50.15 mmol) was placed in a syringe for addition in portions through a septum on the reaction flask. A few drops of triethyl phosphite were added, immediately turning the reaction mixture dark. A pale yellow color rapidly returned, at which point more triethyl phosphite was added. This process was repeated until the color change was no longer observed. At this point another charge of catalyst was added, then more triethyl phosphite. Several additional quantities of catalyst were used. When all the phosphite had been added, the reaction mixture was stirred for a few minutes longer, then cooled to room temperature. Purification was effected by chromatography on silica, eluting with hexanes, followed by 20% ethyl acetate in hexanes, then 30% ethyl acetate in hexanes. The product was obtained as a colorless liquid, 4.84 g, 14.23 mmol, 31% yield. $^1$H NMR (CDCl$_3$) ∂1.33 (m, 6 H), 4.15 (m, 4 H), 7.22 (m, 1 H), 7.77

(m, 1 H), 7.87 (m, 1 H), 8.15 (din, J=13.2 Hz, 1 H); FAB mass spectrum m/z 341 (M+H)⁺.

Example 8

Diethyl [3-(1-tridecynyl)phenyl]phosphonate

Diethyl-3-iodophenylphosphonate prepared according to Example 7 (2.0 g, 5.88 retool) and 1-tridecyne (1.79 g, 9.97 mmol) were dissolved in triethyl amine (40 ml) in a two neck round bottom flask equipped with a condenser and a nitrogen dispersing tube. The flask was inerted. Triphenylphosphine (0.047 g, 0.179 mmol) and palladium acetate ( 0.015 g, 0.0668 mmol) were then added and the flask was heated in an oil bath to 100 to 105° C. for 40 hours. After cooling to room temperature and filtering, the triethylamine was removed on the rotary evaporator. The residue was extracted several times with acetonitrile, and the combined extracts were stripped down to a reddish brown liquid. Chromatography on silica eluting with 20% hexane in ethyl acetate gave the product as a pale yellow oil, 0.410 g, 1.045 retool, 17.7% yield; $^1$H NMR (CDCl$_3$) ∂0.88 (t, J=6.8 Hz, 3 H), 1.18 to 1.50 (several m, 22 H), 1.60 (quint, J=7.6 Hz, 2 H), 2.40 (t, J=7.1 Hz, 2 H), 4.11 (m, 4 H), 7.38 (m, 1 H), 7.55 (br d, J=7.8 Hz, 1 H), 7.71 (dd, J=13.2, 7.6 Hz, 1 H), 7.83 (d, J=14.1 Hz, 1 H); FAB mass spectrum m/z 399 (M+Li)⁺.

Example 9

Tetraethyl [2-[2-(1-tridecynyl)phenyl]ethenylidene] bisphosphonate

In a three neck round bottom flask fitted with an argon inlet, dropping funnel, magnetic stir bar, and septum, tetrahydrofuran (anhydrous, 70 ml) was introduced and cooled to 0° C. Titanium tetrachloride (3.9 ml, 35.6 mmol) dissolved in dry carbon tetrachloride (9.5 ml) was added dropwise over a 30 minute period, producing a copious yellow precipitate. 2-(1-Tridecynyl)benzaldehyde (5.00 g, 17.58 mmol) prepared according to the method described in EP 195 097 A1, which is incorporated by reference herein, was then added via cannula over a ten minute period. A few milliliters of tetrahydrofuran was used to rinse the aldehyde containing flask into the reaction flask. Tetraethylmethylenediphosphonate (5.08 g, 17.62 mmol) was added via cannula over a two to three minute period. N-Methyl morpholine (anhydrous, 7.8 ml, 70.9 mmol) with dry tetrahydrofuran (12 ml) was added dropwise over a forty minute period. The reaction was stirred for four hours and twenty minutes at 0° C. At the end of this time, water (20 ml) was added dropwise over a few minutes to the reaction mixture at 0° C. Ether (25 ml) was added to the mixture which was shaken, and the layers were separated. The aqueous layer was extracted with two more portions of ether (25 ml). The combined organic layers were washed with saturated aqueous sodium chloride solution (25 ml), saturated aqueous sodium bicarbonate solution (25 ml), and with saturated sodium chloride solution (25 ml). After drying (MgSO$_4$), the organic phase was filtered and stripped down to a brown-orange liquid. This liquid was chromatographed on silica (0.57 kg) eluting first with 82% hexane, 13% ethyl acetate, and 5% ethanol, then with 80% hexane, 15% ethyl acetate, and 5% ethanol to give the product as a pale yellow oil, 8.51 g, 15.34 mmol, 87% yield; $^1$H NMR (CDCl$_3$) 0.88 (t, 6.7 Hz, 3 H) , 1.12 (t, J=7.1 Hz, 6 H), 1.20 to 1.48 (m+t, J=7.1 Hz, 22 H), 1.61 (m, 2 H), 2.41 (t, J=7.2 Hz, 2 H), 3.99 (m, 4 H), 4.22 (m, 4 H), 7.30 (m, 2 H), 7.40 (m, 1 H), 7.85 (m, 1 H), 8.54 (dd, J=47.7 Hz, 28.5 Hz, 1 H); HRMS calcd for (M+H)⁺ C$_{29}$H$_{49}$O$_6$P$_2$ m/z 555.3004, found 555.3002.

Example 10

[2-[2-(1-Tridecynyl)phenyl]ethenylidene]bisphosphonic acid

Tetraethyl [2-[2-(1-tridecynyl)phenyl] ethenylidene]bisphosphonate (1.26 g, 2.28 mmol) prepared according to Example 9 was dissolved in a mixture of CH$_2$Cl$_2$-CD$_2$Cl$_2$ (12 ml, 1.73:1). Trimethylsilyl bromide (1.3 ml, 9.85 mmol) was added, and the reaction was stirred for 5 hours. At this time additional trimethylsilyl bromide (0.2 ml, 1.5 mmol) was added. The progress of the reaction was monitored by 1H and $^{31}$p NMR, until no additional change occurred. $^1$H NMR was more useful in this regard, particularly the low field doublet of doublets. At the end of 8 hours, the solvent was removed under reduced pressure and the resulting oil was placed on the vacuum line. Tetrahydrofuran (10 ml) and water (0.25 ml, 13.9 mmol) were added and stirred for 20 hours, then removed under reduced pressure. NMR showed at least two species to be present, so the tetrahydrofuran-water treatment was repeated. After stripping, the residue was recrystallized from heptane as a white solid, 0,793 g, 1.79 mmol, 78.5% yield; mp 141°–142° C.; $^1$H NMR (CD$_3$OD) ∂ 0.89 (m, 3 H), 1.20 to 1.55 (m, 16 H) , 1.63 (quintet, J= 7.4 Hz, 2 H), 2.46 (t, J=7.1 Hz, 2 H), 7.24 to 7.42 (m, 3 H), 7.98 (m, 1 H), 8.42 (dd, J=46.4, 29.0 Hz, 1 H); FAB mass spectrum m/z 443 (M+H)⁺.

Example 11

Disodium [2-[2-(1-tridecynyl)phenyl]ethenylidene] bisphosphonate

[2-[2-(1-Tridecynyl)phenyl]ethenylidene]bisphosphonic acid (0.101 g, 0.228 mmol) prepared according to Example 10 was dissolved in dry tetrahydrofuran (10 ml) and stirred while sodium ethoxide in ethanol (0.177 M, 2.58 ml, 0.457 mmol) was added. After 20 minutes, the solvent was removed under reduced pressure to give a yellowish solid. This solid was pulverized and washed successively with dry ether, tetrahydrofuran, acetone, acetonitrile, and ethanol, then dried on the vacuum line, 0.104 g, 0.214 mmol, 94% yield. $^1$H NMR (D$_2$O) ∂ 0.74 (m, 3 H), 1.17 (m, 14 H), 1.35 (m, 2 H), 1.52 (m, 2 H), 2.39 (t, J=7.1 H, 2 H), 7.24 (m, 2 H), 7.37 (m, 1 H) , 7.92 (dd+m, J=43.8, 27.0 Hz, 2 H); FAB mass spectrum m/z 443 (M−2Na+3H)⁺, 465 (M−Na+2H)⁺, 87 (M+H)⁺.

Example 12

Tetrasodium [2-[2-(1-tridecynyl)phenyl]ethenylidene] bisphosphonate

[2-[2-(1-Tridecynyl)phenyl]ethenylidene]bisphosphonic acid (0.102 g, 0.23 mmol) prepared according to Example 10 was dissolved in dry tetrahydrofuran (10 ml) and stirred while sodium ethoxide in ethanol (0.177 M, 5.19 ml, 0.92 mmol) was added. After 20 minutes, the solvent was removed under reduced pressure to give a light solid. The solid was powdered and washed with dry ethanol, then dried under vacuum, 40.8 mg, 0.084 mmol, 36.5 % yield; mp darkens above 233° C. under N$_2$; $^1$H NMR (D$_2$O) ∂0.89 (m, 3 H), 1.21 to 1.57 (m, 16 H), 1.67 (m, 2 H), 2.55 (t, J=7.1 Hz, 2 H), 7.35 (m, 2 H), 7.51 (m, 1 H), 7.90 (dd, J=42.4, 26.3 Hz, 1 H), 8.19 (d, J= 7.7 Hz, 1 H).

Example 13

Diethyl E-2-[2-(1-tridecynyl)phenyl] ethenylphosphonate

Tetraethyl [2-[2-(1-tridecynyl)phenyl] ethenylidene]bisphosphonate (2.0 g, 3.61 mmol) prepared according to Example 9 was dissolved in tetrahydrofuran (26 ml). Lithium hydroxide (0.152 g, 3.62 mmol) was dissolved in water (10 ml) and added to the tetrahydrofuran solution. After stirring the reaction overnight, ether was added, and the aqueous phase was extracted with ether. The combined ether layers were dried ($MgSO_4$) and stripped down. The residue was chromatographed on silica eluting with 3% ethanol in hexane. Tlc on silica, developed in 5% ethanol in hexane, was used to identify product, $R_f$= 0.04. Impure fractions were combined and rechromatographed as necessary to give 1.21 g, 2.89 mmol, 80% yield of the product as a pale yellow liquid; $^1$H NMR ($CDCl_3$) ∂0.88 (m, 3 H), 1.15 to 1.81 (several m, 24 H), 2.46 (t, J=7.1 Hz), 4.15 (m, 4 H), 6.37 (t, J=18 Hz, 1 H), 7.26 (m, 2 H), 7.42 (m, 1 H), 7.54 (m, 1 H), 7.95 (dd, J=23.0, 17.7 Hz, 1 H); EI mass spectrum m/z 419 (M+H)$^+$.

Example 14

2-[2-(1-Tridecynyl)phenyl]ethenylphosphonic acid

Diethyl E-2-[2-(1-tridecynyl)phenyl]ethenylphosphonate (0.521 g, 1.25 mmol) prepared according to Example 13 was dissolved in $CH_2Cl_2$: $CD_2Cl_2$ (1:1, 9 ml) and stirred while bromotrimethylsilane (0.38 g, 2.48 mmol) was added. The reaction was monitored by $^1$H and $^{31}$p NMR. Additional bromotrimethylsilane (0.1 ml, 0.76 mmol) was added after 6.5 hours. After stirring for 30 hours, the solvent was removed under reduced pressure. Acetone (5 ml) was added, along with water (0.15 ml, 8.3 mmol). The reaction mixture was stirred for about 42 hours, then stripped. NMR indicated that the reaction was incomplete. Acetone (3 ml) and water (0.2 ml, 11.1 mmol) were added back and the reaction was stirred overnight. The solvent was then removed, and the residue was recrystallized from heptane, as a white crystalline solid, 0.348 g, 0.96 mmol, 76.8% yield; mp 82°–83° C.; $^1$H NMR ($CDCl_3$) ∂0.85 (t, J=6.7 Hz, 3 H), 1.10 to 1.45 (m, 16 H), 1.59 (m, 2 H), 2.43 (t, J=7.1 Hz, 2 H), 6.44 (t, J=18.5 Hz, 1 H), 7.26 (m, 2 H), 7.41 (m, 1 H), 7.54 (m, 1 H), 8.04 (dd, J=24.2, 17.6 Hz, 1 H), 10.46 (br s, 2 H); FAB mass spectrum m/z 363 (M+H)$^+$.

Example 15

Tetraethyl [2-[2-(1-Z-tridecenyl)phenyl] ethenylidene] bisphosphonate

Tetraethyl [2-[2-(1-tridecynyl)phenyl] ethenylidene]bisphosphonate (1.5 g, 2.7 mmol) prepared according to Example 9 was dissolved in ethanol (17 ml), and quinoline (0.043 ml) and 5% palladium on calcium carbonate poisoned with lead (13 mg) was added. A balloon filled with hydrogen was attached to the flask after purging with hydrogen. After stirring for 3 hours the hydrogen pressure was released, and the reaction mixture was filtered through Celite. The filtrate was stripped. $^1$H NMR showed that only small amount of starting material had been converted to product. The hydrogenation was repeated using twice the amount of catalyst and quinoline for 4.5 hours, then workup as before. $^1$H NMR showed that a considerable amount of starting material remained. Three additional hydrogenations totaling 47 hours were done before the conversion was greater than 90%. Chromatography on silica eluting with 5% ethanol in petroleum ether (90°–110° C. boiling range) gave the product, 0.459 g, 0.825 mmol, 30.5% yield; $^1$H NMR ($CDCl_3$) ∂0.88 (t, J=6.7 HZ, 3 H), 1.03 to 1.45 (several m, 30 H), 2.09 (m, 2 H), 3.96 (m, 4 H), 4.20 (m, 4 H), 5.79 (dt, J=11.5, 7.4 Hz, 1 H), 6.37 (d, J= 11.4 Hz, 1 H), 7.28 (m, 3 H), 7.78 (d, J=7.3 Hz, 1 H), 8.31 (dd, J=47.8, 28.4 Hz, 1 H); CI mass spectrum m/z 557 (M+H)$^+$.

Example 16

Methyl 3-(2-bromophenyl) -2-E-(diethoxyphosphinyl)-2-propenoate

2-Bromobenzaldehyde (25.89 g, 139.9 retool) and methyl diethyl phosphonoacetate (32.55 g, 148.7 mmol) were combined with piperidine (0.83 ml, 8.4 mmol) and benzoic acid (0.856 g, 7.01 retool) in dry benzene (225 ml). Under argon, this mixture was refluxed for 10.5 days using a Dean-Stark trap to collect the water liberated. At the end of this time, the reaction mixture was cooled to ambient temperature and poured into water (200 ml). The organic layer was washed with water (200 ml), 0.1 N HCl (2×150 ml), water (150 ml), saturated $NaHCO_3$ (2×150 ml), and water (150 ml). After drying ($MgSO_4$), the organic layer was stripped down to an orange-red oil, 41.47 g. This was chromatographed on silica, eluting first with 60:40 petroleum ether (boiling range 37°–52° C.): $CH_2Cl_2$, then with $CH_2Cl_2$, then with hexane-ethyl acetate mixtures to pure ethyl acetate. Fractions containing a spot at $R_f$= 0.06 (silica tlc developed with 68% hexane, 32% ethyl acetate) were combined and rechromatographed on silica eluting with 68% hexane, 32% ethyl acetate. Fractions containing the desired spot were combined and stripped down to a viscous liquid, 25.5 g, 64.85 mmol, 46.4% yield. $^1$H NMR ($CDCl_3$) ∂1.39 (t, J=7.1 Hz, 6 H), 3.68 (s, 3 H), 4.24 (quint, J=7.3 Hz, 4 H), 7.19 to 7.36 (several m, 3 H), 7.61 (dm, J=7.5 Hz, 1 H), 7.85 (d, J= 23.2 Hz, 1 H); EI mass spectrum m/z 377, 379 (M+ H)$^+$.

Example 17

Methyl 3-[2-(1-tridecynyl)phenyl]-2-E-(diethoxyphosphinyl)-2-propenoate

Methyl 3-(2-bromophenyl)-2-E-(diethoxyphosphinyl)-2-propenoate (11.31 g, 29.99 mmol) prepared according to Example 16 was mixed with 1-tridecyne (9.50 g, 52.68 mmol) and triphenylphosphine (0.214 g, 0.82 mmol) in a 500 ml four-neck round bottom flask equipped with a magnetic stir bar, condenser topped with an argon inlet, and an internal thermometer. Dry triethylamine (156 ml) was added, and the flask was closed. The system was inerted and a bubbler was connected to the argon line. Palladium acetate (0.0733 g, 0.33 mmol) was added, and the reaction mixture was heated in an oil bath (T=100 to 105° C). The reaction was refluxed for 50 hours. At the end of this time, the reaction mixture was cooled to room temperature and was filtered. The white precipitate was washed with triethyl amine (100 ml). The filtrates were stripped down to a dark oil. This oil was extracted three times with acetonitrile (50 ml). The combined acetonitrile extracts were stripped down to an orange oil which was chromatographed on silica eluting with petroleum ether-dichloromethane (68:32) increasing to pure dichloromethane, then with hexanes-ethyl acetate (1:1) increasing to pure ethyl acetate. Fractions containing a spot with $R_f$=0.20 on silica developed with hexane-dichloromethane (68:32) were combined and stripped. Reverse phase chromatography on $C_{18}$ silica, eluting with 10% water in methanol, was done. Fractions were combined which showed the above $R_f$. These fractions were rechromatographed on silica eluting with hexanes-ethyl acetate (66:34) and progressing to hexanes-ethyl acetate (60:40). Additional rechromatography of impure fractions gave 4.18 g (8.77 mmol, 29% yield) of pure product as a pale yellow oil. $^1$H NMR (CDCl$_3$) ∂ 0.88 (t, J=6.7 Hz, 3 H), 1.17 to 1.50 (several m, 22 H), 1.63 quintet, J=7.6 Hz, 2 H), 2.43 (t, J=7.2 Hz, 2 H), 3.72 (s, 3 H), 4.21 (m, 4 H), 7.19 to 7.36 (several m, 3 H), 7.44 (dm, J=7.6 Hz, 1 H), 8.05 (d, J=23.8 Hz); EI mass spectrum m/z 476 (M$^+$).

Example 18

Tetraethyl [2-[2-[3-[ (1-oxononyl)amino]-1-propynyl] phenyl]ethenylidene]bisphosphonate A. Preparation of N-Propynylnonanamide Propynylamine (10.4 ml, 151.2 mmol) was mixed with 150 ml of triethylamine in a round bottom flask immersed in a cold water bath, and vigorously stirred while nonanoyl chloride (27.0 ml, 149.75 retool) was added in portions from a dropping funnel over a 30 minute period. Additional triethylamine (100 ml) was added to facilitate stirring. At the end of the addition, the water bath was removed and the reaction was stirred for 30 minutes, then filtered. The filtrate was stripped down to a yellow solid. The solid was partitioned between ether and aqueous NaOH, requiring a considerable quantity of ether to dissolve. The combined ether extracts were stripped and recrystallized from heptane to give product as a white crystalline solid, 18.12 g, 92.8 mmol, 62% yield; top. 78°–79.5° C.; $^1$H NMR (CDCl$_3$) ∂ 0.88 (t, J=6.0 Hz, 3 H), 1.28 (m, 10 H), 1.63 (m, 2 H), 2.19 (t, J=7.6 Hz, 2 H), 2.22 (t, J=2.7 Hz, 1 H), 4.06 (dd, J=5.2, 2.6 Hz), 5.62 (br s, 1 H); EI mass spectrum m/z 196 (M+H)$^+$.

B. N-[3-(2-formylphenyl)-2-propynyl]nonanamide

2-Iodobenzaldehyde (4.06 g, 17.50 mmol) and N-propynylnonanamide (10.12 g, 51.82 mmol) were added to a three neck round bottom flask equipped with an argon inlet and magnetic stir bar, along with cuprous iodide (0.622 g, 3.27 mmol) and tetrakis (triphenylphosphine) palladium (2.0 g, 1.7 mmol). Triethylamine (4.9 ml, 35.6 retool) was added, then anhydrous N,N-dimethylformamide (90 ml). The reaction was vigorously stirred for 2 hours and 50 minutes. At this time 1 ml of 1:1 CH$_{30}$H: CH$_2$Cl$_2$ was added and the solvent was removed under reduced pressure with slight heating (≤40° C.). The dark liquid was partitioned between CH$_2$Cl$_2$ and water. The organic layer was washed several times with water, then dried over K$_2$CO$_3$ and stripped down to an orange-red solid. Chromatography on silica eluting with hexane-ethyl acetate mixtures gave product which was recrystallized from ether-heptane to yield product, 1.21 g, 4.05 mmol, 23% yield; mp 65.5°– 66.5° C.; $^1$H NMR (CDCl$_3$) ∂0.87 (m, 3 H), 1.29 (m, 10 H), 1.67 (m, 2 H), 2.24 (t, J=7.6 Hz, 2 H), 4.35 (d, J= 5.3 Hz, 2 H), 5.78 (br s, 1 H), 7.41 to 7.56 (2 m, 3 H), 7.90 (d, J=7.7 Hz), 10.47 (s, 1 H); CI mass spectrum m/z 300 (M+H)$^+$.

C. Tetraethyl [2-[2-[3-[(1-oxononyl)amino]-1-propynyl] phenyl]ethenylidene]bisphosphonate In a three neck round bottom flask equipped with a magnetic stir bar, argon inlet, and septum, dry tetrahydrofuran (13.5 ml) was added under argon. The flask was placed in an ice bath. Titanium tetrachloride (0.74 ml, 6.75 mmol) was dissolved in dry carbon tetrachloride (1.85 ml), and added to the stirred tetrahydrofuran over a fifteen minute period, producing a bright yellow precipitate. To the stirred mixture, N-[ 3-(2-formylphenyl)-2-propynyl]nonanamide (1.017 g, 3.40 mmol) was added via cannula over a ten minute period, and the flask which contained it was washed with tetrahydrofuran which was added to the reaction. Tetraethylmethylenediphosphonate (0.98 g, 3.4 mmol) was then added over a three minute period. A solution of N-methylmorpholine (1.50 ml, 13.64 mmol) in 2.26 ml of tetrahydrofuran was added over a 45 minute period. After stirring for 3.75 hours at 0° C., water (3.8 ml) was added. The flask was removed from the ice bath and the mixture was extracted with ether (3×12 ml). The ether layers were combined and washed successively with saturated aqueous sodium chloride solution (12 ml), saturated aqueous sodium bicarbonate solution (12 ml), and again with saturated aqueous sodium chloride solution (12 ml). After drying (MgSO$_4$) and filtration, the solvent was stripped off. The residue was chromatographed on silica eluting with 20% isopropanol in ethyl acetate, giving 1.08 g, 1.90 mmol, 55.9% yield of a yellow liquid; $^1$H NMR (CDCl$_3$) ∂0.87 (t, J=6.7 Hz, 3 H), 1.11 to 1.44 (several m, 22 H), 1.66 (m, 2 H), 2.28 (t, J=7.6 Hz, 2 H), 4.03 (m, 4 H), 4.12 to 4.31 (2 m, 6 H), 7.19 (br s, 1 H), 7.38 (several m, 3 H), 7.99 (m, 1 H), 8.71 (dd, J=48.1, 30.1 Hz, 1 H); CI mass spectrum m/z 570 (M+H)$^+$.

The chemical reactions described above are generally disclosed in terms of their broadest application to the preparation of the compounds utilized to practice the method of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The following example demonstrates the effectiveness of the PLA$_2$ inhibitors of the invention utilizing the PLA$_2$ inhibition assays described below.

Example 19

The PLA$_2$ inhibitors of Examples 1–3, 5, 6, 8– 15, 17 and 18 were utilized in the following PLA$_2$ inhibition assays.

The primary assay shows inhibition of purified calcium-independent canine myocardial PLA$_2$. This assay consists of determining the amount of radiolabeled fatty acid which is liberated from the radiolabeled phospholipid substrate by purified calcium-independent canine myocardial PLA$_2$ in the presence of varying concentrations of the inhibitor. The concentration of inhibitor which decreases the activity of the enzyme to 50% of the activity observed in the absence of that inhibitor is determined. This concentration is defined as the IC$_{50}$.

Several other PLA$_2$ assays were also utilized to demonstrate the effectiveness of the PLA$_2$ inhibitors of the invention. Specifically, one micromolar calcium-dependent mammalian PLA$_2$ assay was used, i.e., sheep platelet PLA$_2$, and two millimolar calcium-dependent mammalian PLA$_2$ assays were used, i.e., human synovial fluid PLA$_2$ and porcine pancreatic PLA$_2$. The PLA$_2$ enzymes represent different groups of PLA$_2$ enzymes. Myocardial PLA$_2$, platelet PLA$_2$ and secreted PLA$_2$ enzymes (human synovial fluid PLA$_2$ and porcine pancreatic PLA$_2$) have very different calcium requirements, which may be typical of their respective classes.

An additional whole cell assay was also performed. In this assay, HL-60 cells are induced with the calcium ionophore A23187 in the presence of varying amounts of inhibitor, and the amounts of the prostaglandin E$_2$ (PGE$_2$) and leukotriene B$_4$ (LTB$_4$) which form are measured. Calcium ionophore A23187 activates a calcium-dependent PLA$_2$ which leads to the enhanced production of the arachidonic acid metabolites PGE$_2$ and LTB$_4$. The concentrations of inhibitor which decrease the production of PGE$_2$ and LTB$_4$ by 50% relative to controls are expressed as IC$_{50}$ values. This assay, when inhibition is observed, suggests that the inhibitor enters the cell and inhibits PLA$_2$ or other enzyme in the arachidonate metabolic pathway which produces PGE$_2$ and LTB$_4$.

Calcium-Independent PLA$_2$ Assay

Purified canine myocardial cytosolic PLA$_2$ was isolated from an ATP-agarose eluate as described by Wolf, R. A., and Gross, R. W., *J. Biol. Chem.*, 260, 7295–7303 (1985). The calcium-independent myocardial PLA$_2$ was incubated with selected concentrations ($10^{-10}$ to $10^{-4}$ M) of test compound in 168 mM Tris-Cl, 6.4 mM EGTA (a calcium chelator) (pH 7.0) for 5 min. at 25° C. Appropriate controls were performed in the absence of test compound. Catalysis was initiated by injection of 1 µM radiolabeled substrate (1-O-(Z)-(1'-hexadecenyl)-2-[ 9,10$^{-3}$H]-oleoyl-3-phosphorylcholine). After a 5 min. incubation at 37° C., reaction products were extracted with n-butanol, separated by thin layer chromatography, and quantified by scintillation spectrometry. PLA$_2$ activity was compared in the presence and absence of test compound and the IC$_{50}$ was determined.

Micromolar Calcium-Dependent PLA$_2$ Assay

Homogeneous sheep platelet cytosolic PLA$_2$ was prepared as described by Loeb, L. A., and Gross, R. W., *J. Biol. Chem.*, 261., 10467–10470 (1986). The purified calcium-dependent platelet PLA$_2$ was preincubated in 70 mM Tris-Cl (pH 7.2) containing 1 µM CaCl$_2$ and test compound for 5 min. at 25° C. Catalysis was initiated by injection of 1 µM radiolabeled substrate (1-O-(Z)-(1'-hexadecenyl)- 2-[9,10-3H]-oleoyl-3-phosphorylcholine). After a 10 min. incubation period at 37° C., reaction products were extracted with n-butanol, separated by thin layer chromatography, and quantified by scintillation spectrometry. PLA$_2$ activity was compared in the presence and absence of test compound and the IC$_{50}$ was determined.

While calcium is known to be sufficient for activation of sheep platelet PLA$_2$, it has been found that calcium is not necessary for activation. See Zupan, L. A., et al, "Calcium is sufficient but not necessary for activation of sheep platelet cytosolic phospholipase A$_2$", FEBS Letters, Vol. 284, No. 1, 27–30 (1991).

Millimolar Calcium-Dependent PLA$_2$ Assays

Purified human synovial fluid PLA$_2$ (purified by the procedure of Fawzy, A. A. and Franson, R. C. Biophys. J. 49, 533a [1986]) was obtained from R. C. Franson (Medical College of Virginia, Richmond, Va.). PLA$_2$ activity was measured by using [$^{14}$C]-oleate labeled autoclaved *E. coli* as substrate as described by Franson, R. C., Patriarca, P., and Elsbach, P. J., Lipid Res. 15, 380–388 (1974). The assay was performed at 37° C for 30 min. in a final volume of 100 µL 50 mM Hepes buffer (pH 7.0) containing 150 mM NaCl, 5 mM CaCl$_2$, and *E. coli* cells (corresponding to 10 mmol phospholipid). The test compound or control vehicle was preincubated with PLA$_2$ for 5 min., followed by adding *E. coli* to initiate the reaction. The reaction was terminated by adding 2 mL tetrahydrofuran. The reaction product, [$^{14}$C]-oleic acid, was isolated using a 1 mL Bond Elute—NH$_2$ column and counted by liquid scintillation spectrometry.

Purified porcine pancreatic PLA$_2$ was obtained from Sigma (St. Louis, Mo.). PLA$_2$ activity was measured by using [$^{14}$C]-oleate labeled autoclaved *E. coli* as described by Franson, Patriarca and Elsbach (referenced above). The assay was performed at 37° C. for 5 min. in a final volume of 100 µL Tris-HCl buffer (100 mM, pH 8.0) containing 1 mM EDTA, 10 mM CaCl$_2$, and *E. coli* (containing 10 mmol phospholipid). The test compound or control vehicle was preincubated with PLA$_2$ for 5 min. followed by adding *E. coli* to initiate the reaction. The reaction was terminated by adding 2 mL tetrahydrofuran. The reaction product [$^{14}$C]-oleic acid, was isolated using a 1 mL Bond Elute—NH$_2$ column and counted by liquid scintillation spectrometry.

HL-60 Cell Assay for LTB$_4$ and PGE$_2$ Production

HL-60 cells grown exponentially in culture were induced to differentiate into granulocytes by a four day incubation with 0.8% (v/v) N,N-dimethylformamide. Prior to assay, differentiated HL-60 cells were washed once with Hanks' balanced salt solution containing 0.35 mg/mL sodium bicarbonate and 10 mM Hepes, pH 7.3 (HBSS) and resuspended in HBSS at a 3× 10$^6$ cells/mL concentration. DMSO or test compounds solubilized in DMSO were added at 1:100 dilution to 1.0 mL HL-60 cell suspensions (3×10$^6$ cells) and preincubated at 37° C. for 10 min. in a shaking water bath. After an additional 5 min. incubation with 5× 10$^{-6}$ M calcium ionophore, A23187 (Calbiochem, LaJolla, Calif.), the cells were centrifuged at 12,800×6 for 15 seconds and the supernatant (0.8 mL) removed and stored at −20° C. for LTB$_4$ and PGE$_2$ quantitation by radioimmunoassay (kits obtained from Amersham, United Kingdom and NEN Research Products, N. Billerica, Mass.).

Two conventions are used in Table 1 to indicate an approximate degree of inhibition when an IC$_{50}$ was not reached at the highest concentration of inhibitor: One greater than (>) symbol before the number indicates that inhibition was observed, but not quite enough for an IC$_{50}$. Two greater than symbols (>>) indicate little or no inhibition at the highest concentration used. Activation of an enzyme is indicated by a +X% which gave that activation of X%.

The results in Table 1 illustrate the effectiveness of the compounds of the invention in inhibiting PLA$_2$, specifically calcium-independent PLA$_2$ and micromolar calcium-dependent PLA$_2$ as evidenced by the results of the compounds in the canine heart PLA$_2$ and sheep platelet PLA$_2$ assays.

TABLE 1

| Example No. | Canine Heart PLA$_2$ | Sheep Platelet PLA$_2$ | HSF PLA$_2$ | Porcine Pancreatic PLA$_2$ | HL-60 PGE$_2$ | HL-60 LTB$_4$ |
|---|---|---|---|---|---|---|
| | | | IC$_{50}$ (µM)[c] | | | |
| 1 | 0.56 | 0.18 | >>100 | 100[a] | 3.0 | 1.2 |
| 2 | 0.45 | 11 | 31 | >>100 | >10 | >>10 |
| 3 | 0.36 | 3.2 | 38 | >>100 | >>10 | >>10 |
| 5 | 0.34 | 2.4 | >100 | >>100 | 2.3 | 1.3 |
| 6 | 5.6 | 1.4 | 16 | 2.5 | 3.5 | 4.4 |
| 8 | 0.36 | 0.22 | — | — | — | — |
| 9 | 1.5 | 0.16 | >>100 | — | 4.4 | 2.6 |
| 10 | 0.71 | 50 | 50 | >>100 | >10 | 10[b] |
| 11 | 1.9 | 2.8 | 25 | >>100 | >>10 | >>10 |
| 12 | 2.8 | 7.1 | — | — | — | — |
| 13 | 3.0 | 1.1 | — | — | — | — |
| 14 | 4.5 | 2.9 | — | — | — | — |
| 15 | 1.33 | 0.251 | — | — | — | — |
| 17 | 1.6 | 0.631 | — | — | — | — |
| 18 | >100 | ~100 | — | — | — | — |

[a] +40%
[b] +21%
[c] "—" indicates the compound was not tested.

That which is claimed is:

1. A compound selected from the group consisting of

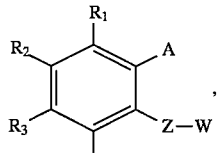

,

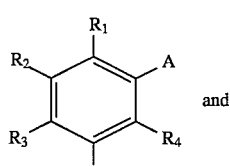

and

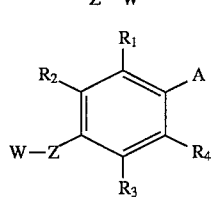

wherein A is represented by the formula

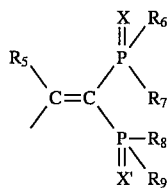

Z is selected from the group consisting of a direct bond and substituted or unsubstituted alkynyl, alkenyl, alkyl and dienyl groups wherein the substituent is selected from the group consisting of —COR, hydroxyalkyl, —SO$_2$R and —P(O)(OR)(OR') groups;

W is selected from the group consisting of hydrogen and substituted or unsubstituted alkyl, alkenyl, alkynyl, aryl, alkaryl and heteroaryl groups wherein the substituent is selected from the group consisting of —COR, hydroxy, halogen, trifluoromethyl, —NHCOR, NR'COR, amino, NR'SO$_2$R and —NHSO$_2$R groups; wherein the sum of the number of carbon atoms in Z and W is at least 3;

R$_1$, R$_2$, R$_3$, R$_4$ and R$_5$ are independently selected from the group consisting of hydrogen, halogen, alkyl, alkenyl, alkynyl, aryl, heteroaryl, alkaryl, alkoxy, thioalkyl, —CHO, —COR, —COOH, —NH$_2$, —NHR, —NRR', —SH, —OH, —COOR, —SO$_2$R, —SOR, —SO$_2$OR, —P(O) (OR) (OR') and —OP(O) (OR) (OR') groups; provided that when one of R$_1$, R$_2$, R$_3$ and R$_4$ is —OH or alkoxy, Z and W contains at least one carbon-carbon double bond or carbon-carbon triple bond;

X and X' are independently selected from the group consisting of oxygen and sulfur atoms; wherein R and R' are independently selected from the group consisting of alkyl, alkenyl, alkynyl, aryl, alkaryl, aralkyl, cycloalkyl, cycloalkenyl and cycloalkynyl groups;

R$_6$ and R$_7$ are independently selected from the group consisting of alkyl, alkenyl, alkynyl, alkoxy, aryloxy, hydroxy, amino, alkylamino, —SH, thioalkyl, thioaryl, halogen and —OM wherein M is a pharmaceutically acceptable cation or R$_6$ and R$_7$ can form a cyclic or bicyclic structure;

R$_8$ and R$_9$ are independently selected from the group consisting of alkyl, alkenyl, alkynyl, alkoxy, aryloxy, hydroxy, amino, alkylamino, —SH, thioalkyl, thioaryl, halogen and —OM or R$_8$ and R$_9$ can form a cyclic or bicyclic structure; and pharmaceutically acceptable salts thereof.

2. The compound of claim 1 wherein at least one of Z and W contains at least one carbon-carbon double bond or carbon-carbon triple bond.

3. The compound of claim 2 wherein Z is alkenyl or alkynyl and W is hydrogen.

4. The compound of claim 3 wherein R$_1$, R$_2$, R$_3$ and R$_4$ are hydrogen.

5. The compound of claim 4 wherein R$_6$, R$_7$, R$_8$ and R$_9$ are independently selected from the group consisting of hydroxy, alkoxy and —ONa.

6. The compound of claim 1 which is tetraethyl [2-[3-(1-tridecynyl)phenyl] ethenylidene]bisphosphonate.

7. The compound of claim 1 which is [2-[3-(1-tridecynyl)phenyl] ethenylidene]bisphosphonic acid.

8. The compound of claim 1 which is disodium [2-[3-(1-tridecynyl)phenyl] ethenylidene]bisphosphonate.

9. The compound of claim 1 which is tetraethyl [2-[2-(1-tridecynyl)phenyl] ethenylidene]bisphosphonate.

10. The compound of claim 1 which is [2-[2-(1-tridecynyl)phenyl] ethenylidene]bisphosphonic acid.

11. The compound of claim 1 which is disodium [2-[2-(1-tridecynyl)phenyl] ethenylidene]bisphosphonate.

12. The compound of claim 1 which is tetrasodium [2-[2-(1-tridecynyl)phenyl] ethenylidene]bisphosphonate.

13. The compound of claim 1 which is tetraethyl[2-[2-(1-Z-tridecenyl)phenyl] ethenylidene]bisphosphonate.

14. The compound of claim 1 which is tetraethyl[2-[2-[3-[(1-oxononyl)amino] -1-propynyl]phenyl]ethenylidene] bisphosphonate.

15. A pharmaceutical composition comprising a therapeutically or prophylactically effective amount of a compound according to claim 1 in a pharmaceutically acceptable carrier.

16. A compound selected from the group consisting of

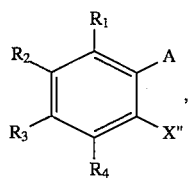

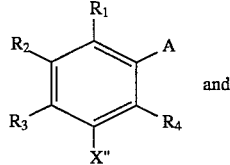 and

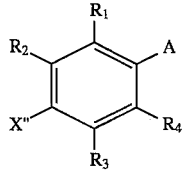

wherein A is represented by the formula

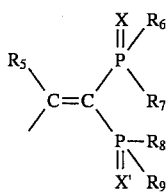

X" is bromine or iodine; provided that when X" is in the meta or para position with respect to A, X" is iodine; X and X' are independently selected from the group consisting of oxygen and sulfur atoms;

$R_1, R_2, R_3, R_4$ and $R_5$ are independently selected from the group consisting of hydrogen, halogen, alkyl, alkenyl, alkynyl, aryl, heteroaryl, alkaryl, alkoxy, thioalkyl, —CHO, —COR, —COOH, —NH$_2$, —NHR, NRR', —SH, —OH, —COOR, —SO$_2$R, —SOR, —SO$_2$OR, —P(O) (OR) (OR') and —OP(O) (OR) (OR') groups; provided that $R_1, R_2, R_3$ and $R_4$ are other than —OH or alkoxy;

wherein R and R' are independently selected from the group consisting of alkyl, alkenyl, alkynyl, aryl, alkaryl, aralkyl, cycloalkyl, cycloalkenyl and cycloalkynyl groups;

$R_6$ and $R_7$ are independently selected from the group consisting of alkyl, alkenyl, alkynyl, alkoxy, aryloxy, hydroxy, amino, alkylamino, —SH, thioalkyl, thioaryl, halogen and —OM wherein M is a pharmaceutically acceptable cation or $R_6$ and $R_7$ can form a cyclic or bicyclic structure;

$R_8$ and $R_9$ are independently selected from the group consisting of alkyl, alkenyl, alkynyl, alkoxy, aryloxy, hydroxy, amino, alkylamino, —SH, thioalkyl, thioaryl, halogen and —OM or $R_8$ and $R_9$ can form a cyclic or bicyclic structure; and pharmaceutically acceptable salts thereof.

17. The compound of claim 16 wherein X" is iodine.

18. The compound of claim 16 wherein $R_1, R_2, R_3$ and $R_4$ are hydrogen.

19. The compound of claim 18 wherein $R_6, R_7, R_8$ and $R_9$ are independently selected from the group consisting of hydroxy, alkoxy and —ONa.

* * * * *